(12) United States Patent
Bari

(10) Patent No.: US 9,381,313 B2
(45) Date of Patent: Jul. 5, 2016

(54) COUNTER FOR A DRUG DISPENSER

(76) Inventor: Naseem Bari, Little Lever (GB)

(*) Notice: Subject to any disclaimer, the term of this patent is extended or adjusted under 35 U.S.C. 154(b) by 38 days.

(21) Appl. No.: 13/260,088

(22) PCT Filed: Feb. 9, 2010

(86) PCT No.: PCT/GB2010/050195
§ 371 (c)(1),
(2), (4) Date: Sep. 23, 2011

(87) PCT Pub. No.: WO2010/112878
PCT Pub. Date: Oct. 7, 2010

(65) Prior Publication Data
US 2012/0012106 A1 Jan. 19, 2012

(30) Foreign Application Priority Data
Mar. 31, 2009 (GB) .................... 0905546.8

(51) Int. Cl.
*A61M 15/00* (2006.01)

(52) U.S. Cl.
CPC .......... *A61M 15/009* (2013.01); *A61M 15/0005* (2014.02); *A61M 15/008* (2014.02); *A61M 2205/8206* (2013.01)

(58) Field of Classification Search
CPC ............... A61M 15/0065; A61M 15/0068; A61M 15/009; A61M 15/005; A61M 15/007; A61M 15/008; A61M 2205/8206
USPC ............. 128/200.14, 200.19–200.23, 203.12, 128/203.14, 203.15, 203.22–203.24, 203.27
See application file for complete search history.

(56) References Cited

U.S. PATENT DOCUMENTS

| | | | | |
|---|---|---|---|---|
| 3,649,787 A | * | 3/1972 | Kasabian | 200/61.45 R |
| 5,363,842 A | * | 11/1994 | Mishelevich et al. | 128/200.14 |
| 5,544,647 A | * | 8/1996 | Jewett et al. | 128/200.23 |
| 6,148,815 A | * | 11/2000 | Wolf | 128/205.23 |

(Continued)

FOREIGN PATENT DOCUMENTS

| EP | 0775499 A2 | 5/1997 |
|---|---|---|
| GB | 2405801 A | 3/2005 |

(Continued)

OTHER PUBLICATIONS

Combined Search and Examination Report under Sections 17 & 18(3) issued in GB0905546.8 application by the United Kingdom Patent Office on Jul. 24, 2009.

*Primary Examiner* — Justine Yu
*Assistant Examiner* — Douglas Sul
(74) *Attorney, Agent, or Firm* — Marshall, Gerstein & Borun LLP

(57) ABSTRACT

The invention is for a waterproof Inhaler Usage Indicator with or without a replaceable battery (6), to provide a count of the amount of drug remaining inside the canister (4) with the counter (1) still attached to the canister (4). It is not limited to inhalers alone, but any type of canister (4) that dispenses through a nozzle (24) when placed inside an housing (2) in order to count the number of displacements between the canister (4) and housing (2). The status of the drug can be checked at any time by a quick movement of the inhaler in any axis to allow the motion sensor (40, 41) to initiate the display of the amount of remaining drug uses. The counter assembly (1) is attached to the top of the canister (4) and uses the displacement between the canister (4) and housing (2) to count the number of uses.

12 Claims, 6 Drawing Sheets

(56) References Cited

U.S. PATENT DOCUMENTS

| | | | |
|---|---|---|---|
| 6,202,642 B1* | 3/2001 | McKinnon et al. | 128/200.23 |
| 6,545,235 B1* | 4/2003 | Chou | 200/61.51 |
| 7,267,847 B2* | 9/2007 | Karamuk | 427/569 |
| 8,215,299 B2* | 7/2012 | Wu | 128/200.23 |
| 2004/0181703 A1* | 9/2004 | Lilja et al. | 713/324 |
| 2004/0255936 A1* | 12/2004 | Urbanus | 128/200.23 |
| 2006/0254581 A1 | 11/2006 | Genova et al. | |
| 2007/0295329 A1* | 12/2007 | Lieberman et al. | 128/200.23 |
| 2008/0060643 A1* | 3/2008 | Hodson et al. | 128/200.23 |
| 2009/0030285 A1* | 1/2009 | Andersen | 600/300 |
| 2009/0151723 A1* | 6/2009 | Lang et al. | 128/203.15 |
| 2012/0055472 A1* | 3/2012 | Brunnberg et al. | 128/203.12 |

FOREIGN PATENT DOCUMENTS

| | | |
|---|---|---|
| GB | 2429922 A | 3/2007 |
| WO | WO-96/03172 A1 | 2/1996 |
| WO | WO-2006/126967 A1 | 11/2006 |
| WO | WO 2008006527 A1 * | 1/2008 |
| WO | WO-2008/142015 A2 | 11/2008 |

* cited by examiner

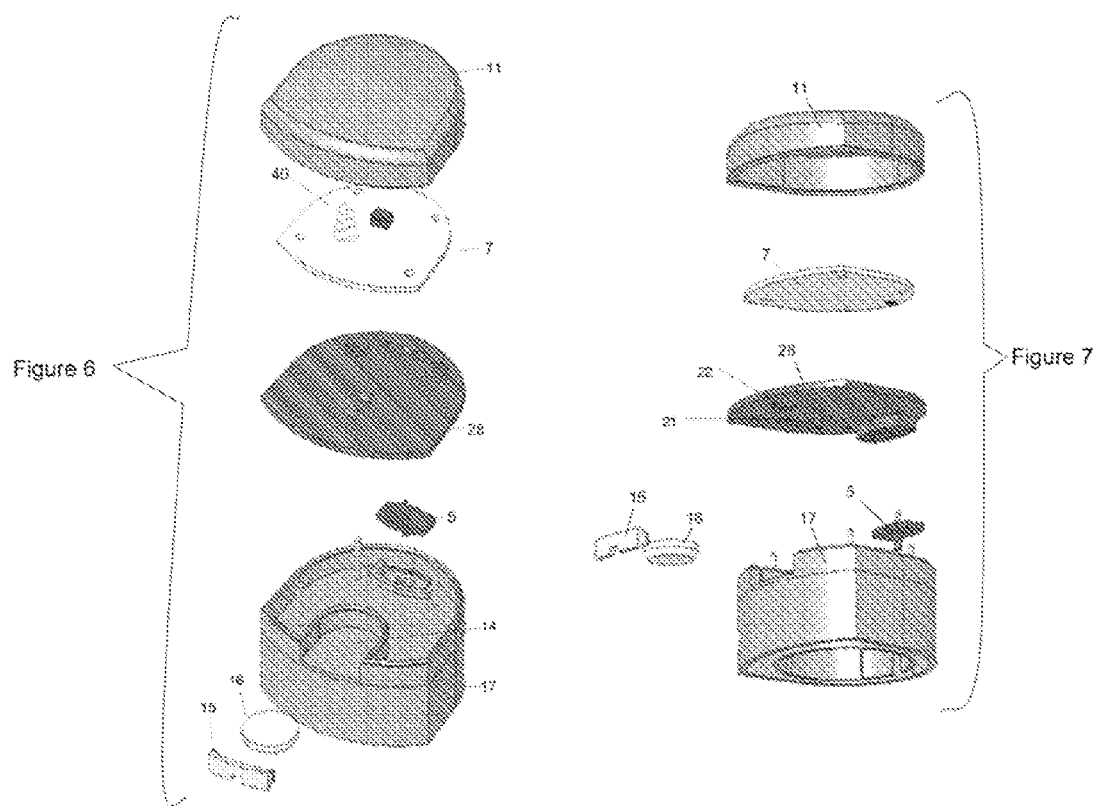
Figure 6
Figure 7
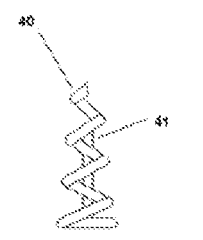
Spring contact expanded view
Figure 8

COUNTER FOR A DRUG DISPENSER

The invention is for a waterproof Inhaler Usage Indicator with or without a replaceable battery, to provide a count of the amount of drug remaining inside the canister with the counter still attached to the canister. It is not limited to inhalers alone, but any type of canister that dispenses through a nozzle when placed inside an housing in order to count the number of displacements between the canister and housing. The status of the drug can be checked at any time by a quick movement of the inhaler in any axis, to allow the motion sensor to initiate the display of the amount of remaining drug uses.

BACKGROUND

Inhalers are commonly used to administer medication such as bronchodilators, corticosteroids and anti-allergenics to the pulmonary tracts of humans and other animals, and in particular to treat nasal and bronchial complaints such as asthma.

A typical inhaler includes a canister, having a nozzle, containing the drug or medicine, and a detachable casing for attachment to the canister. In most applications, the canister contains the drug in powder or liquid form, and the dispensing action forces out a regulated dose of the drug in aerosol form.

The aerosol may be created using a propellant e.g. CFC or HFA forced through the drug by the dispensing motion, or more preferably in PMDIs (pressurised measured-does inhaler) by creation of a significant overpressure inside the canister.

In most PMDIs, the dispensing action consists of moving the canister relative to the casing, the action of the casing on the nozzle of the canister causing the predetermined dose to be released when the nozzle has been depressed a set distance.

Existing inhalers therefore include a detachable casing having a seat member that is engaged with the canister nozzle when the canister is removably inserted to the casing. In most existing inhalers the seat member includes a gripping portion for gripping the nozzle, so that the canister is held in the casting, but only held so that the canister can be easily withdrawn from the casing by simply pulling the canister and casing in opposite directions.

This is the problem that exists. Once the inhaler canister is detached from the housing and mixed with other canisters, for example, to wash the mouth piece out or clean the canister nozzles, there is no means of being able to determine the number of uses that particular canister has left, especially when it is mixed in with other canisters of the same type. It is common for users to have several canisters to ensure that they do not run out of the drug. Keeping count of which canister is still with drugs inside can be a problem.

Typical PMDI canisters for use in PMDIs contain between 60 and 200 doses, and may be used on a daily basis, or only occasionally to relieve particular symptoms. In most cases the patient is unlikely to keep a record of the number of doses administered, so will not be aware when the canister is near to being empty. The patient will not necessarily be immediately aware that the drug is no longer being dispensed when they use the canister as the pressure of the canister, or the dispensing motion, may not change. This could be a potentially serious problem for the patient, resulting in an emergency when they find that the drug in their inhaler had been exhausted by an earlier use. This can cause more anxiety and lead to more emotional distress.

Therefore, there is a need for some form of counting device which can count the number of doses dispensed from a canister to provide an indication of when the canister is empty. In order to be of use, such a counting device must accurately record each actuation of the canister.

Previous attempts to provide such a counting device have had a number of drawbacks. In particular, some solutions have been proposed with a counting device which is mounted on the casing of the inhaler and records each actuation of the canister using, for example, a pressure pad or a lever based switch. These devices suffer from the problem that they either have to be reset manually, or if a canister is removed from the inhaler, the counter automatically resets, so if the same canister is replaced (e.g. after cleaning), the reading will be incorrect.

To overcome this problem, there are many other solutions proposed to try and keep a count of the contents of the remaining drug. However most of these also still have the problem that the count of the drug remains with the housing rather than the canister thus making the design have the same problem that the user still does not know how much is left in the canister should they swap it for another.

These devices can use different techniques but most of them being too costly to manufacture or are too complex in function to allow them to function correctly when mass produced. While these patents are novel in the technique, non of them consider the impact in manufacturing a solution for the public to use the design sufficiently to provide a reasonably accurate indication of the remaining drug.

The design outlined in this patent is to show how an indicator can be designed for manufacture using the manufacturing experience of the Inventor as well as novel design techniques to provide a calibration free design that can be manufactured for the mass market and provide a form of indication to asthmatic users. It is documented that the University of Michigan in 1995 conducted a survey in which it is reported that 54% of asthmatic users do not know the amount of drug remaining in the canister while only 8% actually tracked the amount of usage. It is apparent that major reasons on the lack of designs in the market are precisely because of the cost and complexity of the designs to provide a manufacturability solution. For example the following patents are considered too complex for manufacture:—PCT WO92/17231 by INNOMED shows a set of contact rings on the canister and a set of sensors in the housing. There is no reference to how this would work in the field when you consider calibration, contact problems inside the housing, assembly and user friendly of removing and reinserting the canister. The count is still displayed on the housing rather than on the canister.

Patent US006148815A by James L Wolf shows very complex design built into the housing that will allow to do a number of functions of counting and interfacing to external devices. The one function it does NOT do is to allow the canister to keep the count on the canister so once removed from the housing there is no knowledge of what is left in the canister when reinserted to the housing. Again for manufacture assembly it is very complex and difficult making the unit costly and difficult to use.

EP 0684047 A3 by Walker, William shows a complex counting system attached to the side of the housing and using the vertical displacement of movement of the canister to count. Again housing contains the count while the canister once removed has no means of indication what amount of drug is remaining.

Patent US005411173A by Albert Weinstein shows a spray dispenser. This is similar to the Walker William version except it is upside down for use with an upright spray. The problem again is the complexity to achieve the count and again it does NOT hold the count on the canister when it is removed from the housing.

Patent US006202642B1 by Robert J McKinnon shows a very complex design in which the canister is complexly housed in the housing. Again once removed from the housing there is no count retained by the canister.

Assembly for manufacture is very complex and difficult to use.

Patent WO 02/36190 A2 by Glaxo Group ltd gives a design which incorporates feedback of the drug being released when the dispenser is used. This is accurate but complex to manufacture and calibrate for the user. Again the counter is NOT retained with the canister once removed from the housing.

Patent US005284133A by James S Burns gives a detailed design based on the counter on the housing. Again the count is not retained by the canister once removed from the housing.

The above list is just a few of the designs that have been invented. They all use the relative motion of the canister to the housing to dispense the drug and have numerous ways of indicating the usage. The problem with most of them is that they use the housing to hold the count information rather than the canister. Other patents such as WO 031/103759 A1 by Trumeter company ltd and WO 01/28887 by Glaxo Group Ltd has the indicator on the nozzle and has it assembled onto the front part of the canister. The relative movement of nozzle to this attachment is the method of count. This is an acceptable design but it is complex to manufacture.

All of the designs use power from a battery and do not necessarily disclose the replacement of it and some may be subject to being thrown away after use due to the battery expiring.

SUMMARY OF THE INVENTION

The design herein shows a design that is relatively simple to manufacture while allowing the battery to be replaceable and also retain the count with the canister instead of the housing. It contains a feature that when it is shaken, a motion sensor will be activated and it will initiate an indication of the status of the amount of drug remaining in the canister Accordingly, in its broadest description, the present invention provides a usage counter for a canister assembly including: a canister which has a canister body for containing a substance, for example, a drug, a usage counter assembly which indicates the count and a standard housing which houses the canister assembly such that the top counter assembly engages with the canister housing to count the number of uses, a battery insertion slot, to allow the removal and replacement of the battery while keeping the electronics isolated and waterproofed.

In the event the canister is removed form the standard housing, the usage counter assembly will remain on the canister. In the event the canister is placed accidentally in the water the counter circuit will not be at risk and all that needs to be done is the replacement of the battery. The electronics inside the counter can store the count of the number of drugs dispensed at any time of its use. This can be done in a variety of ways using memory or a special register which contains the usage information.

The design is based on indicating its use by visual means of either a Liquid crystal display (LCD) or preferably a light emitting diode (LED) form when the user uses the inhaler to administer the drug. The display is not limited to electrical means but can also be a mechanical view adjusted by a set of wheels to display the count value. The means of saving power for giving the status of the unit a vibration sensor is used to detect severe side force which will cause an internal electrical contact to be made and so initiate an indication of the LEDs or LCD to display the current usage of the indicator. This technique allows the non use of an external switch keeping the electronics isolated from the external user. It also prevents the drainage of the battery as it will always require a force to cause the indication as a result nothing will happen if it is stationary. Therefore, it is preferable that a canister assembly according to the present invention can be inserted to any standard inhaler casing

BRIEF DESCRIPTION OF THE DRAWINGS

The following figures show the assembly of the counter assembly as follows:

FIGS. 6 and 7 are exploded views of the counter assembly showing all the main parts etc but not the smaller components such as resistor, capacitors etc.

FIG. 8 is an expanded view of a spring contact.

DETAIL DESCRIPTION

Figure 1:
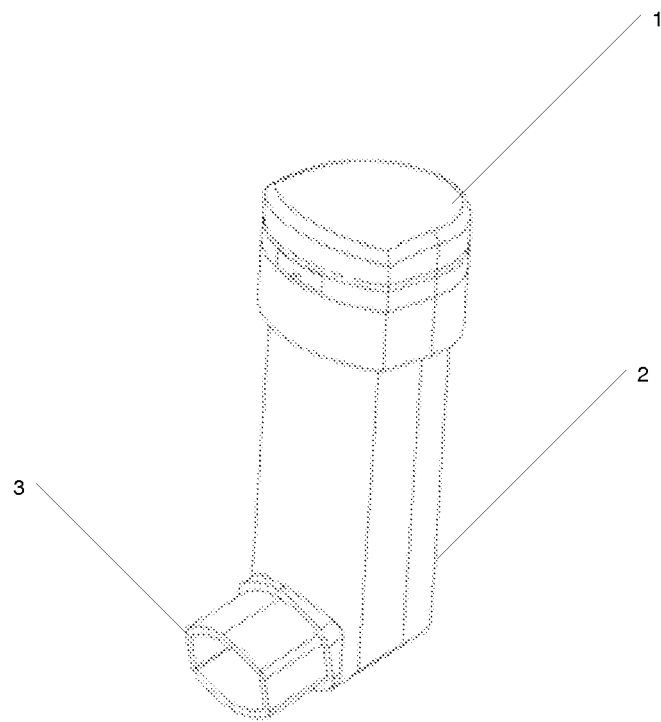
FIG. 1 is a complete system assembly.

With Reference to FIG. 1, this figure shows the fully assembled inhaler unit ready for use. A counter [1] is assembled onto a main housing [2] and in an orientation showing the position of a mouthpiece [3].

Figure 2:
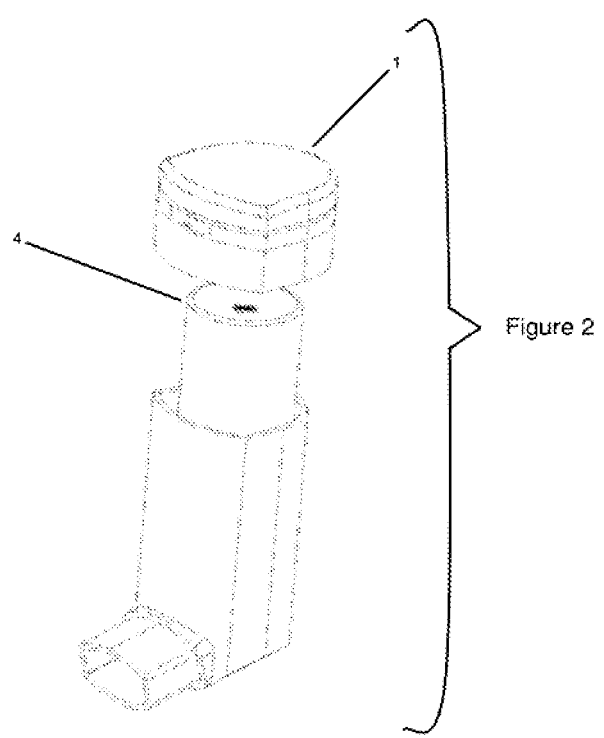
FIG. 2 is an exploded view of the standard housing, canister and counter assembly.

FIG. 2 shows the counter [1] removed from a canister [4], which is inserted into the main housing [2].

Figure 3:
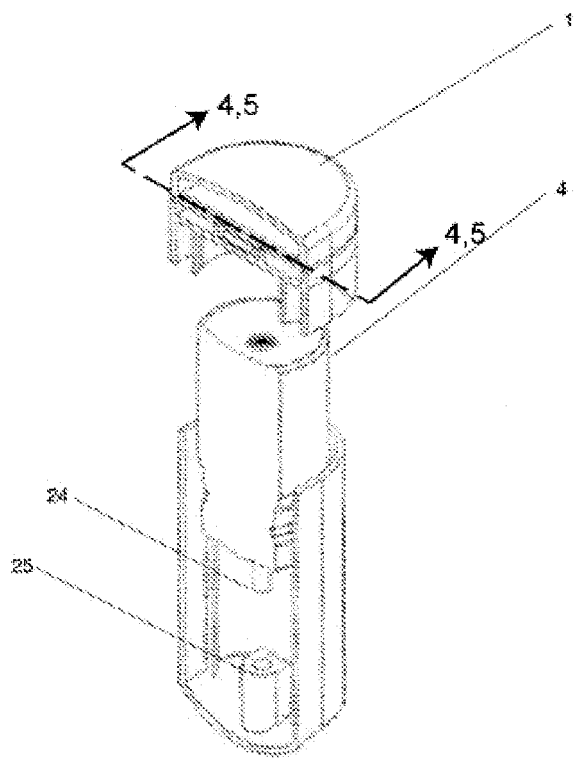
FIG. 3 is across-section cut view showing how the 3 main parts are assembled.

FIG. 3 shows the section view of the full assembly and indicates the coupling of parts. The canister nozzle [24] is inserted into the main housing actuator [25]. Under normal operation the top part of the counter [1] is depressed and the nozzle [24] is depressed into the actuator [25] until a valve inside the canister [4] releases the drug. The drug then disperses through the mouth piece [3].

In this embodiment a tri-colour LED [26] is shown at the top of the counter [1] (see FIG. 4) and the LED would then light up into a magnified dome [27] to indicate successful drug release and indicate the remaining amount of drug in the canister [4].

The current embodiment is based on a traffic light system such that if the number of doses is 200 in the canister, then the LED [26] will change its colour of light based on the amount of drug left. It is preferable that the following table shows the way the light changes colour according to the remaining drug.

Figure 4:
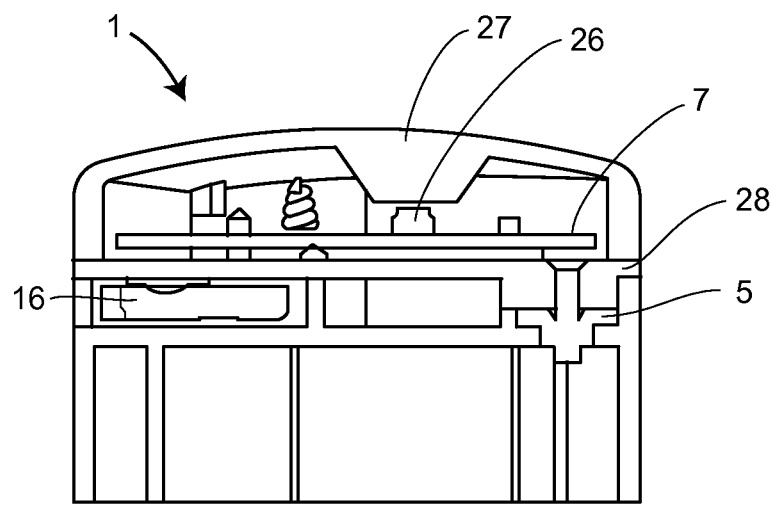
FIGS. 4 and 5 are cross-sections of the main counter assembly.

The LED [26] is shown in FIG. 4 and this can be done instead by using a display to show the numerical use of the canister [4], counting down from 200 or up from 0 to 200, or by a simple means of light changing similar to a traffic light system where a single GREEN flash indicates more than 100 does remaining, single AMBER flash can indicate less than 100 doses remaining and a single RED flash indicates less than 20 doses remaining and the user should think about replacing the canister [4] and a RED flashing many times indicating either empty or less than 5 doses.

Example of Indicator Status:
No of doses more then 100 single LED flashes GREEN
No of doses less then 100 single LED flashes AMBER
No of doses less then 25 single LED flashes RED
No of doses less than 0 3*LED Flashes Red.

The above is an example of the function and the organisation is not set in stone and can be changed to alternative values depending on what the range of doses is present in the canister [4]. Also the choosing of LED [26] colour is a choice by the manufacturer and can be any colour available whether it is a tri-colour LED [26] or single colour LEDs [26] placed together under the magnification dome [27].

A spring [40] and probe [41] assembly provide the function of a motion sensor, in its simplest form, to provide a short circuit to the spring [40] in the event the spring [40] is displaced with side-to-side movement. Any motion sensor can be used but this form allows minimum power to be used to detect vibration or movement in any axis.

In an alternative embodiment an LCD can replace the LED [26] and so a number can be viewable from the dome [27] representing the number of remaining doses.

The choice of embodiment would depend on the user friendliness required. A traffic light system requires no reading and, for children, is much more acceptable by changing colours. Children usually associate with colours much more readily than with text or numbers. Seeing the colour red will make them much aware of danger than a numeral setting.

In a different embodiment, the display means may include at least two or three LEDs [26]. Preferably, the display means includes control means for operating one or more of the LEDs [26] for a predetermined time interval, at a predetermined point in the operation of the device.

The operation of the LEDs [26] for a suitable time after a dose is dispensed from the canister [4] has the advantages of conserving battery life and also serving as an indication that a dose has been dispensed.

Figure 5:
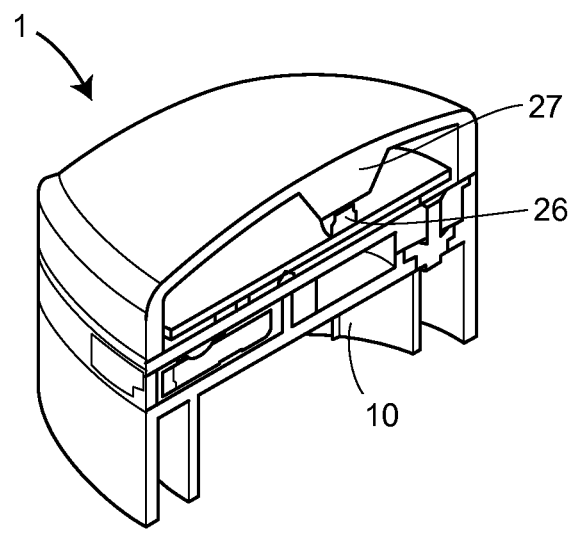

Cross-section views of the counter [1] are shown in FIGS. 4 and 5. These figures give a view of the assembly of the counter [1] and the position of parts within the counter [1].

An elastomeric mat switch [5] is a main switch that will detect the movement of the canister [4] with respect to the housing wall. When this is depressed in it will allow a main processor on a PCB [7] to count the drug and then light the LED [26] with the correct colour.

The length of the switch [5] is dependent on the housing length of the standard housing the canister [4] is placed in. The different housings can be catered for by simply changing the switch [5] dimensions to adjust the length. This makes the counter [1] adaptable to many different shapes without changing the actual functional characteristics of the design. The base can be adjusted so the contour of the base design follows the housing form The switch [5] is held in position by a plate [28] which is ultrasonically welded to a base plate and so as to create a seal against the ingress of liquid.

The plate [28] also has battery connections moulded into it to provide a similar seal against liquid ingress into the counter assembly.

The plate [28] is welded in place to maintain waterproof protection.

Figure 10:
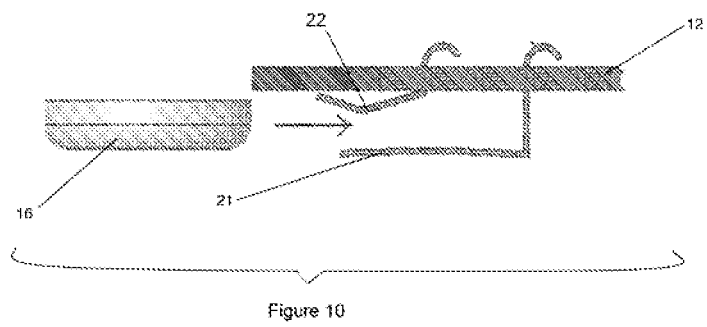
FIGS. 10 and 11 are views showing the insertion of the battery into the counter and the battery cover.
Figure 11:
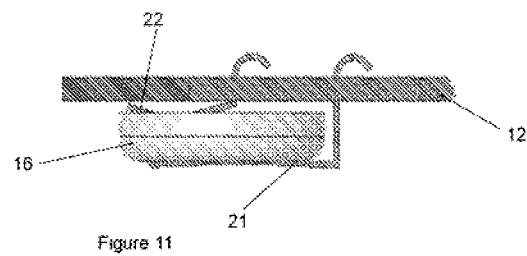
Figure 9:
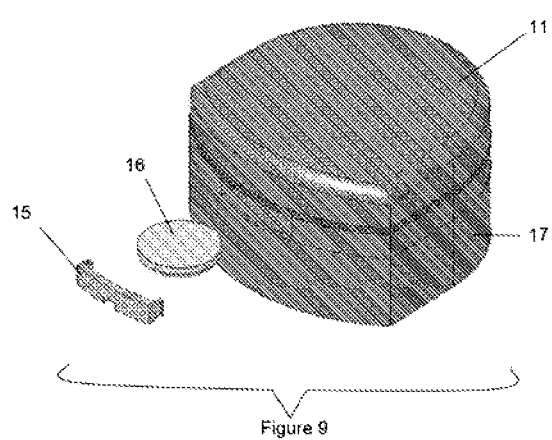
FIG. 9 is an exploded view of the battery assembly.

The base and cover plate together provide a housing for the battery [16] which connects to the PCB [7] using the metal contacts [21, 22] which are welded to the plate and shown in figures given in FIGS. 10 and 11. This design technique allows for the power to be replaced while keeping the electronics isolated from liquid ingress. The battery contact can be made by any conductive material and is not just limited to metal.

The main design function is to provide the electrical connection to the PCB [7] without allowing a path for liquid ingress, but at the same time provide a replaceable power source [16] that allows the counter assembly to be used time and time a gain. FIGS. 10 and 11 show how the battery [16] is inserted into the counter [1] and can be hidden using the battery cover [15] that clips into position.

The whole design is ultrasonically welded together to allow the design to be completely sealed from liquid ingress.

It is known that the water ingress can occur into a battery compartment [14] but the only damage that will occur is that the battery terminals are shorted and this will drain the battery [16]. It will not cause any problem to the actual counter assembly function and the function can be recovered by removing the battery [16] and replacing it with another fresh battery [16]. The battery size is dependant on the power required by the counter assembly and its predicted life time design.

In some uses the battery [16] can be reduced in size to allow a one time function so that it can provide an indication to the user that when a new canister [4] is to be used, a new battery [16] must also be replaced and so there will be no wasted energy. The typical life usage of an inhaler drug can be up to 6 months from first use. This then allows the power calculations to be done in order to match the lifetime of the drug use date.

The user can remove the counter assembly from the canister [4] and reuse it onto another canister [4] due to a friction fit of the counter [1] onto the canister [4]. In this event it is recommended that the user also replaces the battery [16] so that the counter [1] is protected with sufficient power for a normal standard use. The removal is simple as the counter is friction assembled on top of the canister [4].

The battery replacement will re-initialise the counter [1] from initial conditions. The overall function of the counter [1] is to provide a warning when a number of doses equal to the upper limit or the starting number has been dispensed.

Alternative warnings means may also be used, be it audible or visual as shown in this embodiment. Examples of the display can be mechanical display, a clock, LED or an LCD, any of which may display the number of doses dispensed and/or remaining, and may display other information as well, which may, according to the patterns displayed, indicate one or more states of the canister [4] (e.g. full, in use, nearly empty and/or empty).

Thus, in normal use, the status of the canister [4] can be clearly seen or heard.

Preferably, all of the components of the counter switch [5] and display means are sealed within the body.

The PCB [7] contains the electronic Application Specific Integrated Circuit (ASIC) which controls the functions of the counting and display drivers. Other components that are needed such as resistors, capacitors and switches are all on the PCB [7] so that a full electronic function circuit is realised. These electronic components are used in various orientations and locations placed on the PCB [7] so that the space envelope used is minimised and the manufacturability is optimum for cost and ease of assembly.

The counter [1] may comprise a lower housing [17] and an upper housing [11]. The lower housing [17] may define a canister receiving portion [10]. The counter [1] may comprise a lower housing [17] and an upper housing [11]. The lower housing [17] may define a canister receiving portion [10].

It is to be understood that variants of the above described examples of the invention in its various aspects, would be readily apparent to the skilled person, and may be made without departing from the scope of the invention in any of its aspects.

The invention claimed is:

1. A counter and a drug dispenser comprising:
   a canister;
   a canister housing which includes a nozzle through which a predetermined dose of a drug is releasable from the canister, the canister being inserted into the canister housing;
   an arrangement configured to count a number of displacements between the canister and the canister housing;
   a motion sensor which detects vibration, shaking, or movement in any axis;
   a display which indicates how much or how many doses are left in the canister based on the number of counter displacements between the canister and the canister housing, such that the operation of the display is initiated on activation of the motion sensor due to detected vibration shaking or movement in any axis; and
   a counter housing including: a counter housing body in which the arrangement is located, an inner skirt and an outer skirt, the inner skirt extends downwardly from the counter housing main body to form an inner annular wall, which is in a fixed position relative to the remainder of the counter housing, and defines an opening such that the counter housing is mounted with a push-fit fitting on the canister independently of the canister housing, the outer skirt being spaced radially outwardly of the inner skirt and extending downwardly from the counter housing main body to form an outer annular wall, such that an annular channel is defined between the inner and outer skirts, the canister housing being received in the annular channel between the inner and outer skirts, wherein the arrangement includes a switch located within the annular channel and which is actuatable by the canister housing when the canister and counter housing moves relative to the canister housing, wherein the switch forms part of a seal which inhibits the ingress of water into a part of the counter housing containing the arrangement.

2. A counter and a drug dispenser according to claim 1 wherein the counter housing is configured for removal and placement on a new canister.

3. A counter and a drug dispenser according to claim 1 wherein the display operates by emitting light to indicate status of a remaining drug in the canister.

4. A counter and a drug dispenser according to claim 1 wherein the number of counter displacements between the canister and the canister housing is translated to indicate the status of the contents of the canister onto the display.

5. A counter and a drug dispenser according to claim 1, wherein the motion sensor is configured to detect shaking of the counter housing.

6. A counter and a drug dispenser according to claim 5, wherein the motion sensor comprises a spring and probe assembly.

7. A counter and a drug dispenser according to claim 1 that allows replacement of a battery source without affecting a seal property of the counter housing.

8. A counter and a drug dispenser according to claim 7, wherein the seal property of the counter housing is a seal which inhibits the ingress of water into a part of the counter housing containing one or more of a printed circuit board, the motion sensor, and the display.

9. A counter and a drug dispenser according to claim 1 that is waterproof against water ingress into the counter housing.

10. A counter and a drug dispenser according to claim 1, wherein a first end of the canister is inserted into the canister housing and the counter housing is mounted to or adjacent a second end of the canister, the first and second ends of the canister opposing each other across the length of the canister.

11. A counter and a drug dispenser according to claim 1, wherein the arrangement, the display and the motion sensor are housed within the counter housing.

12. A counter and a drug dispenser comprising:
    a canister housing which includes a nozzle through which a predetermined dose of a drug is releasable from a canister, and the canister housing being configured to receive the canister;
    an arrangement configured to count a number of displacements between a canister and the canister housing;
    a motion sensor which detects vibration, shaking, or movement in any axis;
    a display which indicates how much or how many doses are left in a canister based on the number of counter displacements between a canister and the canister housing, such that the operation of the display is initiated on activation of the motion sensor due to detected vibration shaking or movement in any axis; and
    a counter housing including: a counter housing main body in which the arrangement is located, an inner skirt and an outer skirt, the inner skirt extends downwardly from the counter housing main body to form an inner annular wall, which is in a fixed position relative to the remainder of the counter housing, and defines an opening such that the counter housing is mountable with a push-fit fitting on a canister independently of the canister housing, the outer skirt being spaced radially outwardly of the inner skirt and extending downwardly from the counter housing main body to form an outer annular wall, such that an annular channel is defined between the inner and outer skirts, the canister housing being receivable in the annular channel between the inner and outer skirts, wherein the arrangement includes a switch located within the annular channel and which is actuatable by the canister housing when a canister moves relative to the canister housing, wherein the switch forms part of a seal which inhibits the ingress of water into a part of the counter housing containing the arrangement.

\* \* \* \* \*